US00PP28509P2

(12) United States Plant Patent
Renault

(10) Patent No.: US PP28,509 P2
(45) Date of Patent: Oct. 10, 2017

(54) ***HYDRANGEA* PLANT NAMED 'RENBA'**

(50) Latin Name: *Hydrangea paniculata*
Varietal Denomination: RENBA

(71) Applicant: Jean Renault, Gorron (FR)

(72) Inventor: Jean Renault, Gorron (FR)

( * ) Notice: Subject to any disclaimer, the term of this patent is extended or adjusted under 35 U.S.C. 154(b) by 62 days.

(21) Appl. No.: 14/756,844

(22) Filed: Oct. 21, 2015

Related U.S. Application Data

(60) Provisional application No. 62/179,829, filed on May 20, 2015.

(51) Int. Cl.
*A01H 5/02* (2006.01)

(52) U.S. Cl.
USPC ..... Plt./250

(58) Field of Classification Search
USPC ..... Plt./250
See application file for complete search history.

(56) References Cited

PUBLICATIONS

Andre Briant Saison 2014-2015 retrieved on Feb. 2, 2017, retrieved from the Internet at <http://docplayer.net/6633800-Saison-2014-2015-disponible-andre-briant-jeunes-plants-18-07-2014.html> p. 9.*

* cited by examiner

*Primary Examiner* — June Hwu
(74) *Attorney, Agent, or Firm* — Penny J. Aguirre

(57) ABSTRACT

A new cultivar of *Hydrangea paniculata* named, 'RENBA', that is characterized by its upright, well-branched plant habit, its strong, erect branches, its long bloom period, its blooms with panicles of flowers that emerge white in color changing to pink and maturing to a deep pink to red color, and its large and full panicles.

2 Drawing Sheets

Botanical classification: *Hydrangea paniculata.*
Varietal denomination: 'RENBA'.

BACKGROUND OF THE INVENTION

The present invention relates to a new and distinct cultivar of *Hydrangea paniculata* and will be referred to hereafter by its cultivar name, 'RENBA'. 'RENBA' represents a new deciduous shrub grown for landscape use.

The new *Hydrangea* resulted from a controlled breeding program that commenced in 1987 in Gorron, France. 'RENBA' was derived from crosses made in 2007 between unnamed proprietary *Hydrangea paniculata* plants (not patented) from the Inventor's breeding program and the seeds from the crosses where pooled therefore the exact parentage is unknown. 'RENBA' was selected as a single unique plant in 2009 from amongst the resulting seedlings.

Asexual propagation of the new cultivar was first accomplished by softwood cuttings in 2009 by the Inventor in Gorron, France. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish in 'RENBA' as a unique cultivar of *Hydrangea.*

1. 'RENBA' exhibits an upright, well-branched plant habit.
2. 'RENBA' exhibits strong, erect branches.

3. 'RENBA' exhibits a long bloom period, flowering from July to October in France.
4. 'RENBA' exhibits blooms with panicles of flowers that emerge white in color changing to pink and maturing to a deep pink to red color.
5. 'RENBA' exhibits large and full panicles.

'RENBA' can be most closely compared to the *Hydrangea paniculata* cultivars 'RENHY' (U.S. Plant Pat. No. 20,670) and RENSUN (U.S. Plant Pat. No. 25,438). Both cultivars are similar to 'RENBA' in having panicles with flowers that are primarily pink in color during the middle of the bloom season. 'REHNY' differs from 'RENBA' in having branches that are thinner in diameter, in having a more open plant habit, and in having panicles with flowers that remain pink to soft pink in color for the entire bloom season. 'RENSUN' differs from 'RENBA' in having a shorter plant height, in having panicles that are smaller in size, and in having denser branching.

BRIEF DESCRIPTION OF THE DRAWINGS

The accompanying colored photographs illustrate the overall appearance and distinct characteristics of the new *Hydrangea.* The photographs were taken of a 4 year-old plants as grown outdoors in the ground and moved in 25-Liter containers in Gorron, France.

The photograph in FIG. 1 provides a view of the plant habit of 'RENBA' in bloom in September.

Figure 1:
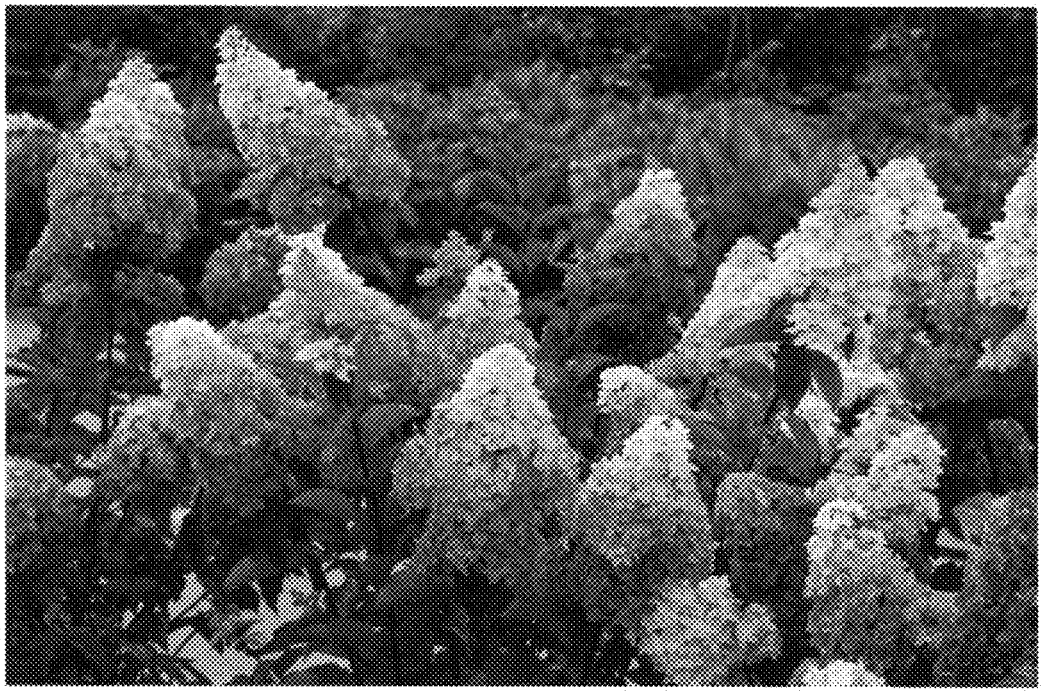
Figure 2:
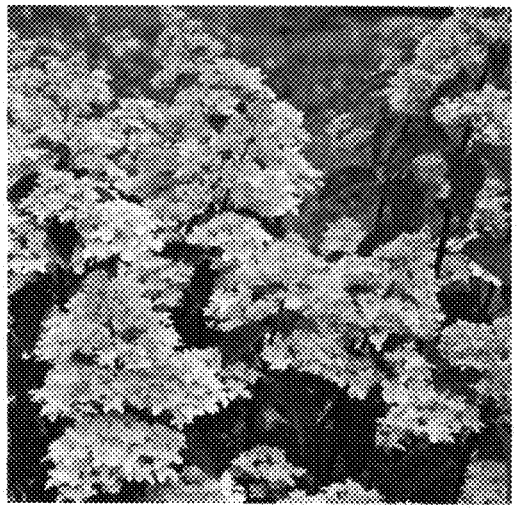

The photograph in FIG. 2 provides a close-up view of inflorescences of 'RENBA' at the beginning of the bloom season.

Figure 3:
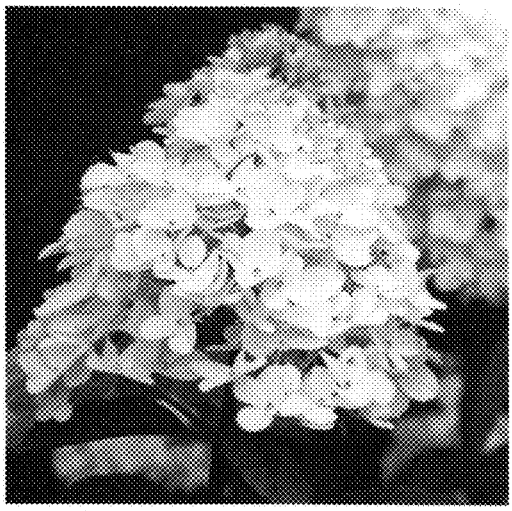

The photograph in FIG. 3 provides a view of the newly opened inflorescences of 'RENBA'.

Figure 4:
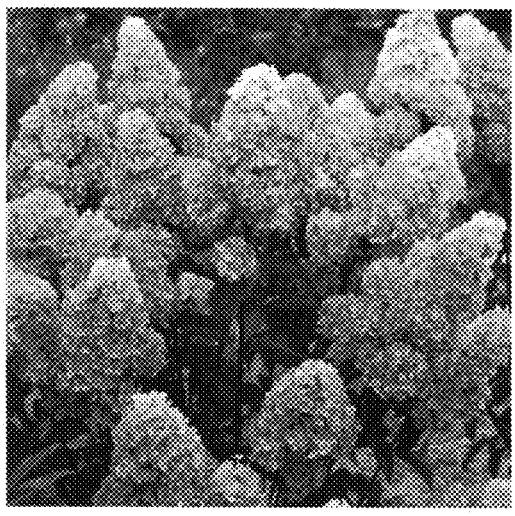

The photograph in FIG. 4 provides a view of the change in inflorescences of 'RENBA' as they are maturing.

Figure 5:
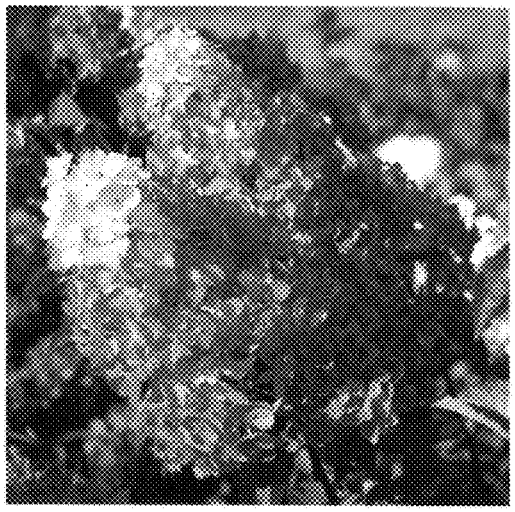

The photograph in FIG. 5 provides a view of the change in inflorescences of 'RENBA' when they are mature.

The colors in the photographs are as close as possible with the photographic and printing technology utilized and the color values cited in the Detailed Botanical Description accurately describe the colors of the new *Hydrangea.*

DETAILED BOTANICAL DESCRIPTION

The following is a detailed description of the new cultivar as observed on 2.5 year-old plants as grown in the greenhouse and outdoors in a 5-gallon container in St. Paul, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—From July to October in France.

*Plant type.*—Herbaceous shrub.

*Plant habit.*—Upright with strong erect stems, well branched.

*Height and spread.*—An average of 2 m in height and 1.5 m width.

*Cold hardiness.*—At least to U.S.D.A. Zone 4.

*Diseases and pests.*—No particular susceptibility and resistance to diseases or pests has been observed.

*Root description.*—Fibrous, 164D in color.

*Propagation.*—Softwood stem cuttings.

*Root initiation.*—About 2 weeks in summer under greenhouse conditions without supplemental lighting and about 3 weeks in winter with bottom heat in France.

*Time required to produce a salable crop.*—A plug of a rooted cutting finishes in a P9 container grown outdoors in about 5 to 6 months.

*Growth rate.*—Vigorous.

Stem description:

*Shape.*—Round, solid.

*Stem color.*—New wood 178B, mature wood a blend of 200A, 200B, and 152A with flaky bark a blend of 200B and N200B, old wood (dormant); a blend of N199C, 201A, and 201B.

*Stem diameter.*—New branches, average of 5 mm on average, old wood; average of 1.3 cm in recorded 5 cm from base of plant.

*Stem surface.*—Pubescent when young becoming flaky on mature first years wood, and moderately roughed barked on old wood.

*Internode length.*—Average of 4 cm.

*Branching.*—7 mature branches per crown on a 2-year old plant, average of 4 lateral branches per mature branch, subsequent branching is determined by pinching.

Foliage description:

*Leaf shape.*—Elliptic.

*Leaf division.*—Simple.

*Leaf base.*—Rounded.

*Leaf apex.*—Primarily acuminate.

*Leaf venation.*—Pinnate, slightly recessed on upper surface, color N144A on upper and suffused on midrib towards base 178B, N148C on lower surface with mid rib lightly suffused towards base with 178B.

*Leaf margins.*—Serrated.

*Leaf attachment.*—Petiolate.

*Leaf arrangement.*—Opposite.

*Leaf surface.*—Very sparse hairs on upper and glabrous on lower surface.

*Leaf color.*—Newly formed and mature leaves upper surface; a color between 147A and 146A, newly formed leaves and mature leaves lower surface; 148B.

*Petioles.*—Average of 2 cm in length and 2 mm in width, slightly sulcate in shape, stipules absent, 178B in color.

Flower description:

*Inflorescence type.*—Broadly pyramidal panicles of sterile and fertile florets.

*Lastingness of inflorescence.*—Persistent but color is retained for 6 to 8 weeks before browning.

*Inflorescence size.*—Average of 16 cm in length and 12 cm in width.

*Inflorescence number.*—One per stem, new shoots develop throughout the summer.

*Flower number.*—An average of 250 sterile flowers and 200 fertile flowers per inflorescence.

*Fragrance.*—Slightly when newly opened.

*Flower size.*—Sterile flowers; average of 3 cm in diameter and 8 mm in depth, fertile flowers; average of 6 mm in diameter and 5 mm in depth.

*Flower buds.*—Sterile flowers: globose in shape, average of 4 mm in length and 3.5 mm in width, N155B in color with very apex flushed with 62A, fertile flowers; globose in shape, up to 3 mm in length and 2.5 mm in width, NN155B in color, glabrous surface for both.

*Peduncles.*—Average of 1.7 cm in length and 2 mm in width, 145B in color, pubescent surface, held at an average angle of 45°, strong.

*Pedicels.*—Sterile flowers; moderate strength, an average of 1.5 cm in length and 1.5 mm in width, 145B in color, surface is pubescent, held at variable angles to peduncle, average of 2 petiole leaves; narrowly oblanceolate in shape, about 3 mm in length and 1 mm in width, glabrous on both surfaces, truncate base, acuminate apex, 145B in color, fertile flowers; and average of 3 mm in length and 1 mm in width, strong, pubescent surface, pedicel leaves (1 to 2) minute if present and match all other characteristics of sterile flower pedicels.

*Fertile flowers.*—Rotate in shape, lasting about 7 days on the plant, only pistils, ovary and sepals persistent, petals; 5, narrowly elliptic in shape, N155B on both surfaces, about glabrous on both surfaces, acute apex, truncate base, average of 4 mm in length and 1.5 mm in width, sepals; 5 fused in campanulate calyx, average of 1.5 mm in length and 2 mm in width, fared free triangular-shaped tips about 0.4 mm in width and length, 157A in color and glabrous on both surfaces.

*Sepals (sterile flowers).*—4 (rarely 5), un-fused, very slightly to non overlapping, rotate in arrangement, smooth, dull and glabrous on both surfaces, broadly elliptic to broadly ovate in shape, held slightly upwards when fully open, primarily entire margin with occasional undulations or serrations, apex is rounded to broadly acute, average of 1.5 cm in length and 1.4 cm in width, color of upper and lower surfaces: when newly open N144A and changing to 155B and becoming flushed with 62B, color of upper and lower surfaces when maturing; a blend of 157A and 145A and flushed with 62A (more prominently on upper surface), color when mature upper surface; 59A to 59D, color when mature lower surface; 59A and 59B, fall color both surfaces; a blend of 145C, N199B and 199C.

*Eye of sterile flowers* (*petal spot*).—1.5 mm in diameter, 1 mm in depth, 155B and suffused with 62A in color, quickly drop as flowers mature.

Reproductive organs (present on fertile flowers):

*Stamens*.—Average of 10, anther is 1 mm in length and 198D in color, filament is an average of 3 mm in length and N155B in color, pollen is low in quantity and N155B in color.

*Pistils*.—Average of 3, average of 4 mm in length and 145D in color, style is an average of 2 mm in length and 145B in color, stigma is club shaped and N155B in color (newly opened blooms), ovary is an average of 1.5 mm in diameter and 145B in color.

*Fruit and seed*.—None observed to date.

It is claimed:

1. A new and distinct cultivar of *Hydrangea* plant named 'RENBA' as herein illustrated and described.

* * * * *